US00PP29980P2

(12) United States Plant Patent
O'Connell

(10) Patent No.: US PP29,980 P2
(45) Date of Patent: Dec. 11, 2018

(54) ***ECHEVERIA* PLANT NAMED 'CALYPSO'**

(50) Latin Name: ***Echeveria* hybrid**
Varietal Denomination: Calypso

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/732,293

(22) Filed: Oct. 19, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Echeveria* cultivar named 'Calypso' is disclosed, characterized by concentric rosettes comprised of an abundance of ruffled blue-green leaves with crispate margins. The new cultivar is robust growing, quickly filling an 8 inch commercial pot and produces offsets at an early maturity. Plants have been shown to be durable with good landscape performance. Inflorescences are produced in the Summer, comprised of glaucous coral colored flowers. *Echeveria* is a popular genus, typically produced as container plants for the patio or as landscape plants, as a variety of ornamental purposes.

2 Drawing Sheets

Latin name of the genus and species: *Echeveria* hybrid. Variety denomination: 'CALYPSO'.

BACKGROUND OF THE INVENTION

The new cultivar, *Echeveria* 'Calypso', is the product of a planned breeding program. The new variety originated from a cross pollination of the proprietary, unpatented, seed parent, *Echeveria* 'BF II' with the pollen parent an unpatented, proprietary variety of *Echeveria* referred to as 'Val'. The cross pollination was made during May of 2013 in Vista, Calif., at a commercial greenhouse. The new cultivar 'Calypso' was discovered by the inventor, Renee O' Connell, in April of 2014, in Vista, Calif. at a commercial greenhouse.

Asexual reproduction of the new cultivar 'Calypso' was first performed in Vista, Calif., at a commercial greenhouse, by terminal vegetative cuttings in May of 2014. *Echeveria* 'Calypso' has since produced multiple generations and has shown that the unique features of this cultivar are stable and reproduced true to type.

SUMMARY OF THE INVENTION

The cultivar 'Calypso' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CALYPSO'. These characteristics in combination distinguish 'CALYPSO' as a new and distinct *Echeveria* cultivar:

1. The rosettes of *Echeveria* 'Calypso' are comprised of many ruffled blue-green leaves, arranged in an attractive concentric rosette, as compared to many *Echeveria* cultivars used for larger pot sizes which produce rosettes with less leaves, and often of a less saturated shade of blue gray.
2. *Echeveria* 'Calypso' grows to a diameter of 14" or more, often producing offsets to form clusters at approximately 7" of diameter
3. The leaves of *Echeveria* 'Calypso' are a rich blue green color, and display undulate, crispate pink margins, creating an attractive an attractive contrast between leaf color and the margin color.
4. A single cut of *Echeveria* 'Calypso' readily fills an 8" pot, thereby reducing the number of cuttings required to fulfill a grow schedule for a 8" pot in a commercial production setting.
5. *Echeveria* 'Calypso' produces inflorescences during the summer, with individual flowers a glaucous coral in color, with inner golden tangerine tips, flaring outward apically, and becoming orange basally.
6. *Echeveria* 'Calypso' is a moderately fast grower, enhancing production times in the commercial nursery environment.
7. *Echeveria* 'Calypso' is robust plant, and as such, has proven durable in the landscape environment.

PARENTAL COMPARISON

Plants of the new cultivar 'Calypso' can be compared to plants of the unpatented, proprietary seed parent *Echeveria* 'BF II', and are similar in most horticultural characteristics. However, plants of the new cultivar 'Calypso' differ in the following:

1. *Echeveria* 'Calypso' forms rosettes that are flatter in morphology than those of *Echeveria* 'BF' II'.
2. *Echeveria* 'Calypso' exhibits leaves that are a rich blue-green color, whereas the leaves of *Echeveria* 'BF II' are a glaucous powder blue.

3. *Echeveria* 'Calypso' forms flowers that are glaucous coral in color, with inner golden tangerine tips, flaring outward apically, and becoming orange basally, whereas the flowers of *Echeveria* 'BF II' express a two-toned appearance, coral basally, and golden yellow apically.
4. *Echeveria* 'Calypso' displays leaves that are slightly wider than those of *Echeveria* 'BF II', becoming wider and blunter apically than those of *Echeveria* 'BF II'.
5. While both *Echeveria* 'BF II' and *Echeveria* 'Calypso' display undulate, crispate leaves, the leaves of *Echeveria* 'Calypso' differ additionally in the apical aspect in that they are 'truffly', whereas the apical portion of the leaves of *Echeveria* 'BF II' is apiculate.

Plants of the new cultivar 'Calypso' can be compared to plants of the unpatented, proprietary pollen parent *Echeveria* 'Val', and are similar in most horticultural characteristics. However, plants of the new cultivar 'Calypso' differ in the following:

1. *Echeveria* 'Calypso' displays rosettes comprised of many rich blue-green leaves, whereas *Echeveria* 'Val' produces rosettes of darker blue, tinged with violet in strong light.
2. *Echeveria* 'Calypso', begins to offset at approximately 6-7" of diameter, whereas *Echeveria* 'Val' is reticent to offset.
3. The flowers of *Echeveria* 'Val' are slightly larger than those of *Echeveria* 'Calypso', and whereas the flowers of *Echeveria* 'Calypso' are glaucous coral in color, with inner golden tangerine tips, flaring outward apically, and becoming orange basally, the flowers of *Echeveria* 'Val' are light gold and do not flare appreciably at the apex.

COMMERCIAL COMPARISON

The new cultivar 'Calypso' can be compared to the unpatented commercial variety *Echeveria* 'Afterglow'. Plants of the *Echeveria* 'Afterglow' are similar to plants of the new cultivar 'Calypso' in most horticultural characteristics. However, the new cultivar 'Calypso' differs in the following:

1. *Echeveria* 'Calypso' forms rich blue green rosettes, whereas the rosettes of *Echeveria* 'Afterglow' are violet in color.
2. *Echeveria* 'Calypso' exhibits spatulate leaves that are wider at the tip, whereas the leaves of *Echeveria* 'Afterglow' are more or less lanceolate in shape, and display little to no crispate margins.
3. *Echeveria* 'Calypso' displays flowers that are glaucous coral in color, with inner golden tangerine tips, flaring outward apically, and becoming orange basally, whereas the flowers of *Echeveria* 'Afterglow' are a solid orange in color.

The new cultivar 'Calypso' can be compared to the unpatented commercial *Echeveria subrigida*. Plants of *Echeveria subrigidas* are similar to plants of the new cultivar 'Calypso' in most horticultural characteristics. However, plants of the new cultivar 'Calypso' differ in the following:

1. *Echeveria* 'Calypso' produces rosettes of a rich blue green color, whereas the rosettes of *Echeveria subrigida* are a pruinose blue or near white.
2. *Echeveria* 'Calypso' produces rosettes of many leaves, whereas *Echeveria subrigida* produces rosettes with less leaves.
3. *Echeveria* 'Calypso' produces more compact rosettes than does *Echeveria subrigida*.
4. *Echeveria* 'Calypso' displays wider, more apically rounded leaves as compared with the longer leaves produced by *Echeveria subrigida*, in conjunction to the more compact morphology of *Echeveria* 'Calypso', thereby rendering it much less prone to leaf breakage when shipping specimens.
5. *Echeveria* 'Calypso' displays flowers that are glaucous coral in color, with inner golden tangerine tips, flaring outward apically, and becoming orange basally, whereas the flowers of *Echeveria subrigida* are a monotone golden orange in color.

BRIEF DESCRIPTION OF THE PHOTOGRAPHS

The accompanying photographs illustrate in full color typical of plants of *Echeveria* 'Calypso' grown in a greenhouse in Vista, Calif. Age of the plant photographed is approximately 7 months from a terminal vegetative cutting. The photograph was taken using conventional techniques and although colors may appear different from actual colors due to light reflectance it is as accurate as possible by conventional photographic techniques. All photographs provided by the breeder.

DETAILED BOTANICAL DESCRIPTION

Figure 1:
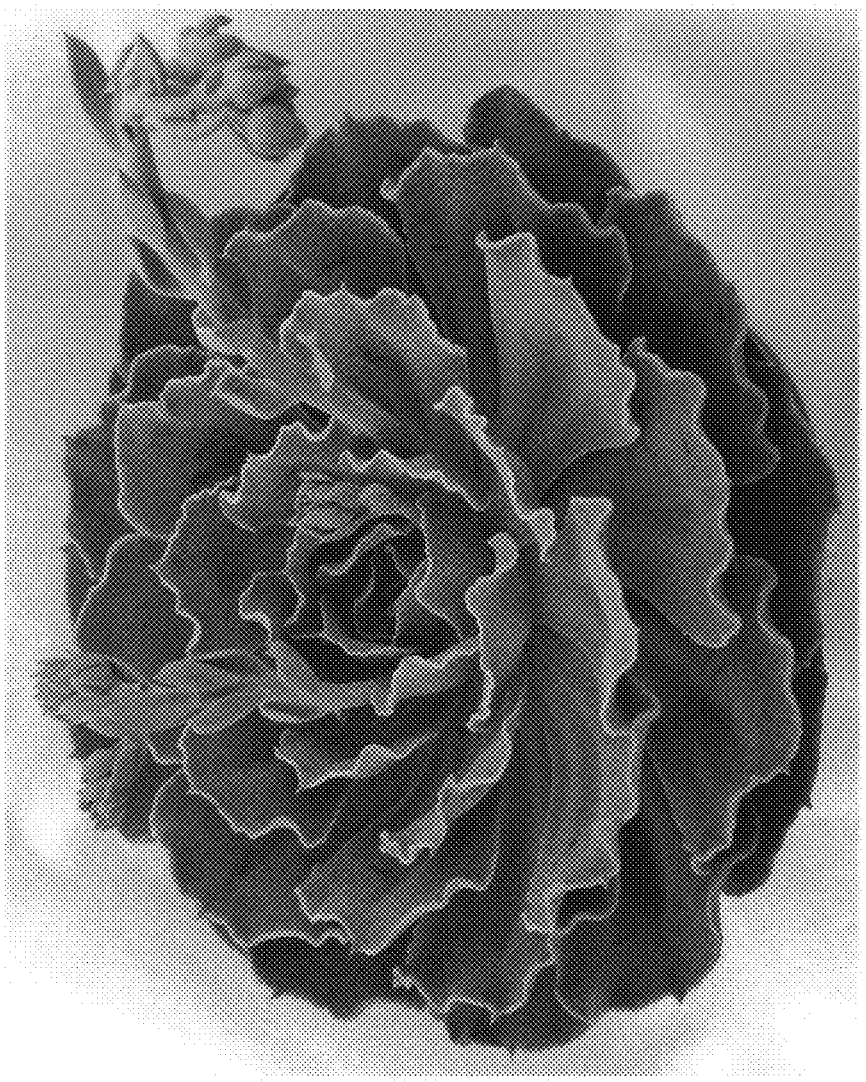
FIG. 1 illustrates in full color the top view of a rosette typical of plants of *Echeveria* 'Calypso' grown in a greenhouse in Vista, Calif.
Figure 2:
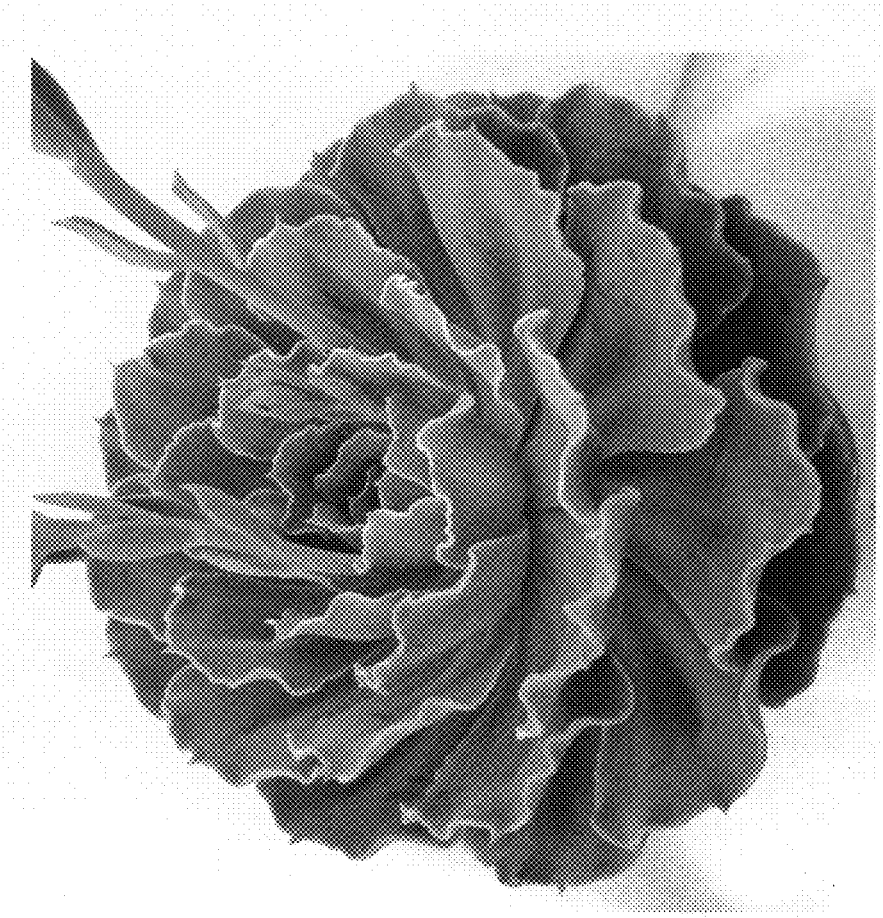
FIG. 2 illustrates in full color the side view of a rosette typical of plants of *Echeveria* 'Calypso' grown in a greenhouse in Vista, Calif.

In the following description, color references are made to The Royal Horticultural Society Colour Chart, 2007, except where general terms of ordinary dictionary significance are used. The following observations and measurements describe 'Calypso' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'CALYPSO'.

PROPAGATION

Type of propagation typically used: Terminal vegetative cuttings.

Time to initiate roots: About 11 days at approximately 24° C.

Root description: Fibrous.

PLANT

Age of plant described: Approximately 4 months from a cutting.

Container size of the plant described: 1 gallon.

Growth habit: Densely and somewhat flattened rosulette plant.

Height: Approximately 13 cm to top of highest leaf. Approximately 30 cm to 45 cm to top of highest inflorescence.

Plant spread: Approximately 28.0 cm.

Growth rate: Rapid.

Branching characteristics: Not typically observed.

FOLIAGE

Leaf:
*Arrangement*.—Rosulate.
*Average length*.—Average range 9.5 to 12 cm.
*Average width*.—6.1 cm.
*Widest width*.—Approximately 8.0 cm.
*Width at base*.—Average 2.6 cm.
*Thickness of leaf*.—Thickest section, near base 2 mm.
*Shape of blade*.—Spatulate.
*Apex*.—Blunt rounded obtuse, nearly truncate with a single, small mucronate tip, approximately 3 to 4 mm long. Irregular, broad crenation along entire apex.
*Base*.—Broad attenuate.
*Margin*.—Entire towards base, upper margin crispate.
*Texture of top surface*.—Slightly to moderately glaucous.
*Texture of bottom surface*.—Slightly to moderately glaucous.
*Appearance of top surface*.—Matte.
*Appearance of bottom surface*.—Matte.
*Quantity of leaves per plant*.—Average range 50 to 65.

Color:
*Young foliage upper side*.—Near RHS Greyed-Green 191B. Very fine apical margin coloration near Yellow-Green 150D, slightly flushed Orange-Red N34C. Glaucous layer over entire surface colored near Greyed-Green 189D.
*Young foliage under side*.—Near RHS Greyed-Green 191B. Very fine apical margin coloration near Yellow-Green 150D, slightly flushed Orange-Red N34C. Glaucous layer over entire surface colored near Greyed-Green 189D.
*Mature foliage upper side*.—Near RHS Greyed-Green 191B. Strong apical margin coloration near Red 46C. Glaucous layer over entire surface colored near Greyed-Green 189D.
*Mature foliage, under side*.—Near RHS Greyed-Green 191B. Strong apical margin coloration near Red 46D. Glaucous layer over entire surface colored near Greyed-Green 189D.

FLOWER

Natural flowering season: Summer.
Inflorescence type and habit: Erect, composed of several simple or bifurcate cincinni, each cincinnus typically with 6 to 9 flowers and about 10 buds.
Rate of flower opening: About 3 to 7 days from bud stage to open flower, depending on environmental conditions.
Flower longevity on plant: 4-7 days, depending upon ambient temperatures.
Quantity of flowers: About 20 to 40 individual flowers and 30 to 60 buds.
Total inflorescence size:
*Height*.—Approximately 12 to 20 cm.
*Width*.—Approximately 10 to 16 cm.

Corolla:
*Arrangement*.—Pentagonal, fused.
*Size*.—Length: Approximately 1.8 cm. Width: Approximately 1.1 cm at widest point. Lobe Length: Approximately 0.7 cm. Lobe width: Approximately 0.4 cm.

Petals:
*Margin*.—Entire.
*Shape*.—Unfused section deltate.
*Apex*.—Acute.
*Base*.—Fused, approximately ¾ entire length.
*Texture*.—Glabrous.
*Color*.—When opening: Petal color, outer surface: Near RHS Red 43C, slightly glaucous when immature, glaucous coloration near N187D. Inner surface: Center near Red 51D, margin 52A, apex yellow 12B. Fully opened: Outer surface: Near Red 52B. Very find apical margin near Yellow 12A. Overall slight glaucous covering near Red 36D. Inner surface: Apex near Red 36A, apex Yellow 2C. Color Changes when Aging: Flower contracts, making inner surface impossible to see. Outer surface Orange-Red N34C, upper section near N34B.

Bud: (near opening):
*Shape*.—Conical.
*Length*.—Approximately 1.7 cm.
*Diameter*.—Approximately 1.3 cm.
*Color*.—Near Red 48A, lightly flushed Red 53C.

Sepals:
*Length*.—7 to 11 mm.
*Width*.—3 to 4 mm.
*Margin*.—Entire.
*Shape*.—Deltate.
*Apex*.—Acute.
*Base*.—Truncate.
*Texture*.—Glabrous, upper and lower surfaces.
*Appearance*.—Matte, slightly glaucous, upper and lower surfaces.
*Color*.—Outer: Near RHS Greyed-Green 189A. Inner: Near RHS Greyed-Green 189A.

Peduncle:
*Length*.—Average range 18 to 22 cm.
*Width*.—Approximately 1.0 cm.
*Strength*.—Strong.
*Texture*.—Glabrous.
*Color*.—Near RHS Greyed-Green 191C.

Pedicels:
*Length*.—Approximately 1.1 cm.
*Width*.—Approximately 0.3 cm.
*Strength*.—Strong, flexible.
*Texture*.—Glabrous.
*Color*.—Near RHS Greyed-Red 181C.

Fragrance: None detected.

REPRODUCTIVE ORGANS

Stamens: (Androecium).
*Number*.—Average 10.
*Filament length*.—Approximately 0.5 cm.
*Filament color*.—Near RHS White N155D.
*Anther length*.—0.3 cm.
*Anther color*.—Near RHS Greyed-Yellow 162B.
*Anther shape*.—Oblong.
*Pollen color*.—Near RHS Yellow 10B.
*Pollen quantity*.—Scant to moderate.

Pistil: (Gynoecium).
*Number*.—Average 5.
*Length*.—Approximately 1.2 cm.
*Style color*.—Near White N155D.

*Stigma*.—Shape: Linear. Color: Near S RHS 187A. Ovary Color: Near RHS White 155C.

OTHER CHARACTERISTICS

Fruits and seeds: Typical to Genus. Minute, less than 1 mm dry seeds. Colored between black and brown, too small to accurately measure with color chart.

Temperature tolerance: Tolerates temperatures from approximately −2° C. to at least 35° C.

Disease/pest resistance: Neither resistance or susceptibility to normal diseases and pests of *Echeveria* has been observed.

Drought tolerance: Tolerates at least 3 weeks of high temperatures without supplemental water, showing no serious damage to plant.

What is claimed is:

1. A new and distinct cultivar of *Echeveria* plant named 'CALYPSO' as herein illustrated and described.

* * * * *